Figure 1:
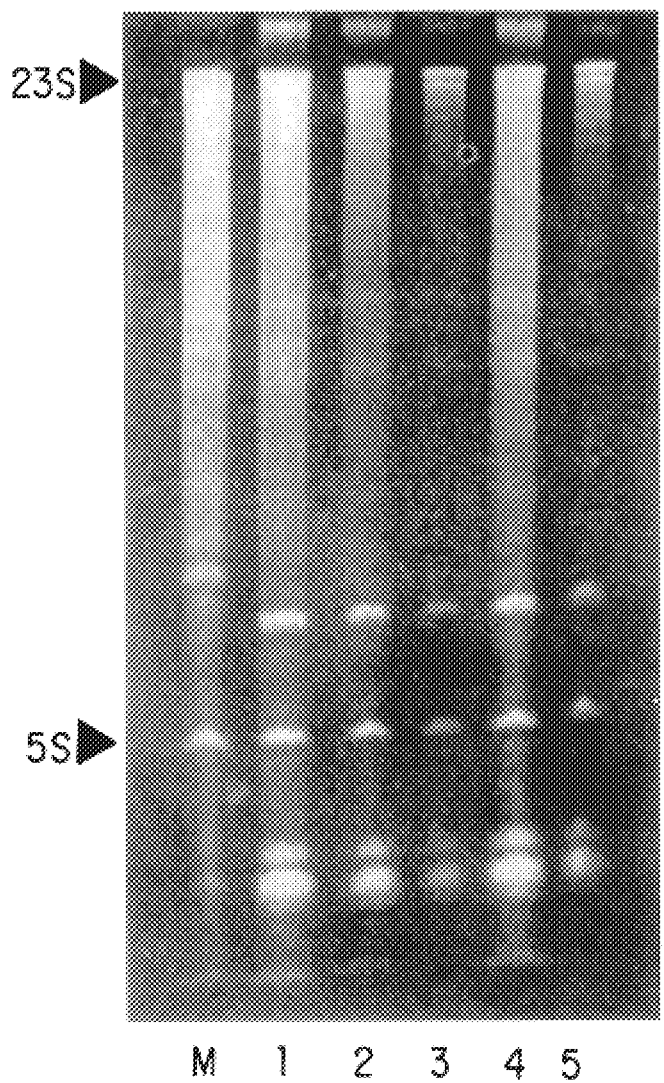

United States Patent [19]
Breitenbach et al.

[11] Patent Number: 5,837,550
[45] Date of Patent: Nov. 17, 1998

[54] METHOD FOR SCREENING AN EXPRESSION CDNA CLONE BANK FOR THE DETECTION OF POLYNUCLEOTIDES

[75] Inventors: Michael Breitenbach; Dietrich Kraft; Helmut Rumpold, all of Vienna; Otto Scheiner, Mariaenzersdorf; Heimo Breiteneder; Karin Pettenburger, both of Vienna; Rudolf Valenta, Theresienfeld, all of Austria

[73] Assignee: Biomay Produktions-Und Handelsgesellschaft m.b.H., Linz, Austria

[21] Appl. No.: 255,127

[22] Filed: Jun. 7, 1994

Related U.S. Application Data

[63] Continuation of Ser. No. 59,197, May 5, 1993, abandoned, which is a continuation of Ser. No. 353,844, May 18, 1989, abandoned.

[30] Foreign Application Priority Data

Oct. 14, 1988 [AT] Austria ................................. 2554/88

[51] Int. Cl.$^6$ .......................... G01N 33/563; C07K 16/16
[52] U.S. Cl. ....................... 436/513; 436/512; 530/388.5
[58] Field of Search .................... 436/512, 513; 530/388.5

[56] References Cited

U.S. PATENT DOCUMENTS 4,721,668 1/1988 Jones, III et al. ........................... 435/6

OTHER PUBLICATIONS

Fang et al., Proc. Natl. Acad. Sci. (USA) 85:895–899 (1988).
Breiteneder et al., Int. Arch. Allergy Appl Immunol 87:17–24 (1988).
Lauzurica et al., "Olive (*Olea Europea*) Pollen Allergens–I. Immunochemical Characterization by Immunoblottin, Crie and Immunodetection by a Monoclonal Antibody," Mol. Immunol. 25(4): 329–335 (1988).
Sutton et al., "Detection of IgE and IgG–Binding Proteins After Electrophoretic Transfer from Polyacrylamide Genes," J. Immunol. Meth. 52:183–194 (1982).
Helfman, D., and S. Hughes, 1987, "Use of Antibodies to Screen cDNA expression Libraries Prepared in Plasmid Vectors", *Methods of Enzymology* 152:451–458.
Hatton et al., "Identification of cDNA Clones Representing Group I Pollen Allergens from Kentucky Bluegrass", in *Allergy and Molecular Biology,* A. El Shami and T. Merrett eds., Pergamon Press, Oxford. (Jan. 1989).
Davis et al., *Microbiology* (J.B. Lippincott, Philadelphia) 4th Edition (1990).

Ipsen, H. and Hansen, O.C. in: *Epitopes of Atopic Allergens.* Sehon, A.H., Kraft, D., Kunkel, G. (eds) (1990) UCB, Brussels, Belgium, pp. 3–8.
Rumpold, et al. In: *Epitopes of Atopic Allergens.* Sehon, A.H., Kraft, D., Kunkel, G. (eds) (1990) UCB, Brussels, Belgium, pp.; 26–28.
Valenta, et al. In: *Epitopes of Atopic Allergens.* Sehon, A.H., Kraft, D., Kunkel, G. (eds) (1990) UCB Brussels, Belgium, pp. 73–76.
Florvaag, E. et al. Int. Arch. Allergy Appl. Immunol. 75:300–308 (1984).
Florvaag, E. et al. Int. Arch. Allergy Appl. Immunol. 67:49–56 (1982).
Jarolim, et al. Int. Arch. Allergy Appl. Immunol. 90:54–60 (1989).
Hatton, T.W., Hill, R.D., Ekramoddoullah, A.K.M., Kisil, F.T. and Sehon, A.H., "Molecular Cloning of Kentucky Bluegrass (KBF) Pollen Allergens," *J. Allergy Clin. Immunol.*, (Jan. 1988) 81(1), Zusammenfassung [abstract] Nr. 58, siehe den ganzen Artikel, Siete p. 183.
Lütck, H.A. et al. EMBO J. 6(1):43–48 (1987).
Thomas et al. In: *Epitopes of Atopic Allergens.* Sehon, A.H., Kraft, D., and Kunkel, G. (eds), 1990. UCB Institute of Allergy, Brussels.
Nagai, K. et al. Nature 309:810–812 (1987).
Stinson, J.R. et al. Plant Physiol. 83:442–447 (1987).
Walter, M.H. et al., Proc. Natl. Acad. Sci. USA 85:5546–5550 (Aug. 1988).
Rogers, B. et al., International Publication WO 90/11293, published 4 Oct. 1990, entitled: "Allergenic proteins from ragweed and uses therefore".
Valenta, R. et al. J. Allergy Clin.Immunol. 88(6):889–894 (1991).
Stratagene Cloning Systems 1992 Product Catalog, Cloning Vectors: pBluescript II, pp. 30–31.
Stratagene Technical Profile of pBluescript II Phagemid.
Tchang et al. J. Biol. Chem. 263(32):16849–16855 (1988).
Crawford et al. Proc. Natl. Acad. Sci. USA 83:8073–8076 (1986).
Reed et al. Proc. Natl. Acad. Sci. USA 85:7661–7665 (1988).

*Primary Examiner*—Michael P. Woodward
*Attorney, Agent, or Firm*—Pennie & Edmonds LLP

[57] ABSTRACT

The invention relates to a method by which expression cDNA clone banks are screened by means of IgE antibodies derived from the sera of allergic individuals, or by means of monoclonal or polyclonal antibodies. This type of screening is used for the detection of polynucleotides whose open-reading frames code for allergenically active proteins. These proteins are characterized in that their biological activity as allergens is equal to that of plant allergens occurring in nature.

2 Claims, 12 Drawing Sheets

FIG. 10A

```
  1
  agtatcggcggatcc TGTTCTAATTCCATTTATCACATCCAATTAAAAATCTCTCAGGCCATC
                                                                64

65  ATG  GCT  GTT  TTC  AAT  TAC  GAA  ACT  GAG  ACC  TCT  GTT  ATC  CCA  GCA   112
     Met  Gly  Val  Phe  Asn  Tyr  Glu  Thr  Glu  Thr  Ser  Val  Ile  Pro  Ala   16
      1

113  GCT  CGA  CTC  TTC  AAG  GCC  TTT  ATC  CTT  GAT  GGC  GAT  AAT  CTC  CCA   160
     Ala  Arg  Leu  Phe  Lys  Ala  Phe  Ile  Leu  Asp  Gly  Asp  Asn  Leu  Pro   32
     17

161  AAG  GTT  GCA  CCC  CAA  GCC  ATT  AGC  AGT  GTT  GAA  AAC  ATT  GAA  GGA   208
     Lys  Val  Ala  Pro  Gln  Ala  Ile  Ser  Ser  Val  Glu  Asn  Ile  Glu  Gly   AAT
     33                                                                          Asn 48

209  GGA  CCT  GGA  ACC  ATT  AAG  AAG  ATC  AGC  TTT  CCC  GAA  GGC  TTC        256
     Gly  Pro  Gly  Thr  Ile  Lys  Lys  Ile  Ser  Phe  Pro  Glu  Gly  Phe        CCT
     49                                                                          Pro 64

257  TTC  AAG  TAC  GTG  GAC  GAC  GAC  AGA  GAT  GAT  GAG  GTC  GAC  CAC  ACA   304
     Phe  Lys  Tyr  Val  Asp  Asp  Asp  Arg  Asp  Asp  Glu  Val  Asp  His  Thr   TTC
     65                                                                          Phe 80

305  AAA  TAC  AAT  TAC  AGC  GTG  ATC  ATC  GAG  GAG  GGT  GGC  CCC  ATA  GGC   352
     Lys  Tyr  Asn  Tyr  Ser  Val  Ile  Ile  Glu  Glu  Gly  Gly  Pro  Ile  Gly   TTG
     81                                                                          Leu 96
```

| 353 | 356 | 359 | 362 | 365 | 368 | 371 | 374 | 377 | 380 | 383 | 386 | 389 | 392 | 395 | 398 | 400 |
|---|---|---|---|---|---|---|---|---|---|---|---|---|---|---|---|---|
| GAG | AAG | ATC | TCC | AAC | GAG | ATA | AAG | ATA | GTG | GCA | ACC | CCT | GAT | GGA | | GGA |
| Glu | Lys | Ile | Ser | Asn | Glu | Ile | Lys | Ile | Val | Ala | Thr | Pro | Asp | Gly | | Gly |
| 97 | | | | | | | | | | | | | | | | 112 |

| 401 | | | | | | | | | | | | | | | | 448 |
|---|---|---|---|---|---|---|---|---|---|---|---|---|---|---|---|---|
| TCC | ATC | TTG | AAG | ATC | AGC | AAC | AAG | TAC | CAC | ACC | AAA | GGT | GAC | CAT | | GAG |
| Ser | Ile | Leu | Lys | Ile | Ser | Asn | Lys | Tyr | His | Thr | Lys | Gly | Asp | His | | Glu |
| 113 | | | | | | | | | | | | | | | | 128 |

| 449 | | | | | | | | | | | | | | | | 496 |
|---|---|---|---|---|---|---|---|---|---|---|---|---|---|---|---|---|
| GTC | AAG | GCA | GAG | CAG | GTT | AAG | GCA | AGT | AAA | GAA | ATG | GGC | GAG | ACA | | CTT |
| Val | Lys | Ala | Glu | Gln | Val | Lys | Ala | Ser | lys | Glu | Met | Gly | Glu | Thr | | Leu |
| 129 | | | | | | | | | | | | | | | | 144 |

| 497 | | | | | | | | | | | | | | | | 554 |
|---|---|---|---|---|---|---|---|---|---|---|---|---|---|---|---|---|
| TTG | AGG | GCC | GTT | GAG | AGC | TAC | CTC | TTG | GCA | CAC | TCC | GAT | GCC | TAC | | AAC |
| Leu | Arg | Ala | Val | Glu | Ser | Tyr | Leu | Leu | Ala | His | Ser | Asp | Ala | Tyr | | Asn |
| 145 | | | | | | | | | | | | | | | | 160 |

545 TAA TTAATTAACTTGTGTCGTCTCGAACATGTCCCTGATCAATAATGGGTTGCAGTGTTCATG 607
END

608 GTGTTTTTGGGTCTAATAAAGGAGCTTGCAGTTGTGATCATCTGCTTGCTAGCTGAAGATGTT 671

672 GTAATTTGTTGGGAGAATGATAATAAATGTCTATTAAAAAAAAAAAAAAAAAAAAAAAAAAA 735

736 AAAAAAAA 744
Aggaattcc

FIG.10B

METHOD FOR SCREENING AN EXPRESSION CDNA CLONE BANK FOR THE DETECTION OF POLYNUCLEOTIDES

This is a continuation of application Ser. No. 08/059,197, filed May 5, 1993, now abandoned, which in turn is a continuation of application Ser. No. 07/353,844, filed May 18, 1989, now abandoned.

1. INTRODUCTION

The invention relates to a method for screening an expression CDNA clone bank for the detection of polynucleotides which in their open reading frames code for proteins whose biological activity as allergens is equal to that of plant allergens occurring in nature.

2. BACKGROUND OF THE INVENTION

At some time in their lives, at least 10% of the population suffers from pollen allergies to varying degrees. In the pollen season patients complain of itching in the nose, itchy and reddened eyes, running nose, swollen eyelids, and very frequently of cough and asthmatic symptoms. Mainly light, wind-borne pollen gets into the mucous membranes of the eyes and the respiratory system of man, is in some cases broken down locally and, in genetically disposed patients (so-called allergic individuals), lead to sensitization and thus to elevated production of IgE antibodies active against a variety of proteins in pollen. In the months of February to April, pollen from trees such as, for example, alder, hazelbush and birch predominates, in May, June and July pollen from grasses and grains, and in July and August pollen from weeds such as mugwort, plantain, sorrel and goosefoot, predominates. On repeated contact, pollen proteins (allergens), by combining with IgE molecules on the surface of mast cells in mucous membranes, cause a release of inflammatory substances such as histamine, leukotrienes, chemotactic factors, platelet-activating factor (PAF), among others, and result in a typical clinical picture (hay fever, pollen asthma) termed a type I allergic reaction.

The effects of a pollen allergy, ranging from unpleasant to dangerous, have for decades been treated with anti-inflammatory drugs and/or by means of so-called hyposensitization. The latter consists of the administration of pathogenic pollen proteins in gradually increasing doses in the form of injections or, with children, in the administration of drops until a distinct decrease in symptoms is obtained (commencement of tolerance). Because of its success, this form of immunotherapy is accepted as the basis of any therapy of pollen allergy with pronounced symptoms. However, a good outcome for such treatments requires that a diagnosis, including skin tests, serological tests and the like, be made with precisely defined pollen extracts, and that treatment with the proteins triggering the pollen allergy be administered at adequate concentrations that have to be exactly determined. Until now, pollen proteins have been obtained by the collection of pollen by costly methods, where it should be considered that, as a rule, the pollen collected represents a mixture of a wide variety of plant pollen, which then has to be separated, purified and processed in costly procedures. In addition, it is virtually impossible to obtain large quantities of a pure pollen protein by the known methods. That is, proteins eliciting an allergy are present on and in pollen in a great variety of concentrations, often depending upon climate, time of year and weather. Therefore, when non-standardized extracts are used, in many cases patients' individual conditions receive too little attention, which is reflected in poor therapeutic results.

3. SUMMARY OF THE INVENTION

The object of the invention is to provide a method of the type mentioned above by which the allergens responsible for allergic reactions or the polynucleotides coding for them can be detected in a simple and specific way.

Pursuant to the invention, this object is accomplished in that proteins expressed in the expression cDNA clone bank are identified by means of IgE antibodies derived from sera of allergic individuals. Those proteins and the polynucleotides coding for them which are responsible for the allergic reaction are identified.

Identification may alternatively be made by polyclonal or monoclonal antibodies, whereby those proteins or the polynucleotides coding for them which are homologous with those triggering the allergic reactions are identified.

The CDNA clone coding for the major birch pollen allergen, Bet v I, to be described below is highly homologous (55% sequence identity, no gaps) to a pea disease resistance response gene. The pea gene is silent in healthy tissue but heavily expressed upon contact with plant pathogens. It is expected that this highly conserved gene can be used to protect transgenic plants against pathogens.

4. BRIEF DESCRIPTION OF THE FIGURES

FIG. 1. RNA characterization on 6% polyacrylamide-50% urea gel. Lane M: marker. Lanes 1–5: independent RNA isolations from male inflorescences.

Figure 2:
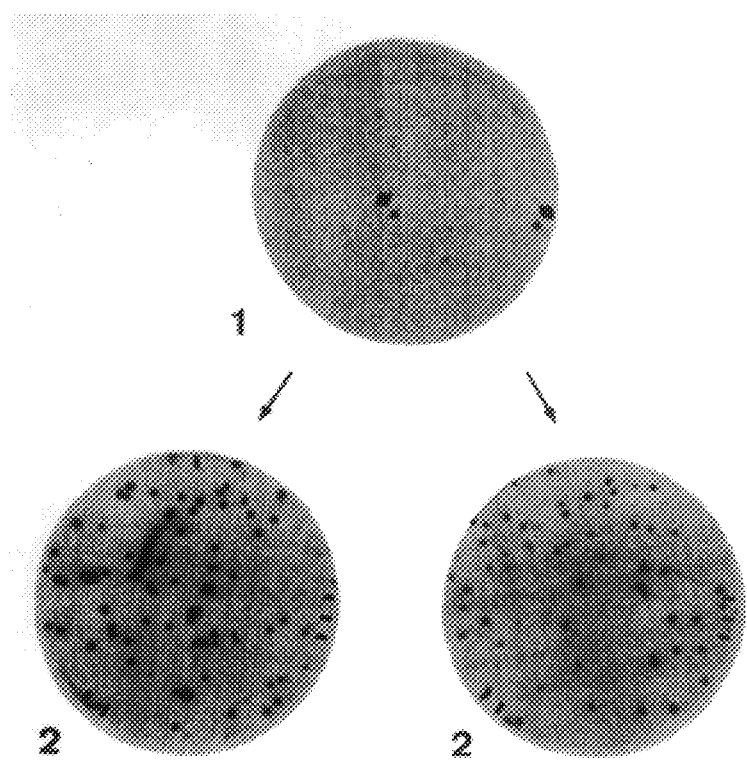

FIG. 2. Detection of positive insert-bearing clones by means of IgE antibodies from the serum of allergic subjects.

Figure 3:
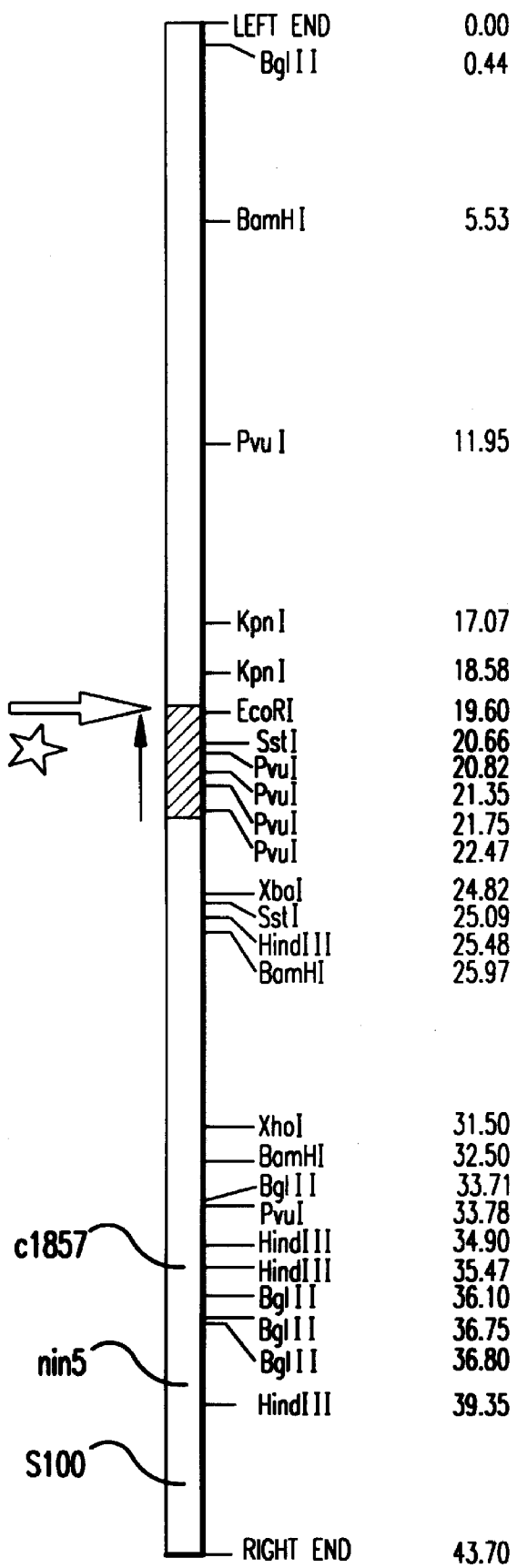

(1) First detection step: 2 positive clones (arrow) continued further (2) Recloning of positive clones FIG. 3. Restriction map of the phage λgt11. Arrow (with star) marks the insertion site for the cDNA.

FIGS. 4A–4B FIG. FIG. 4A.

Lane 1: λgt11 DNA with insert (KpnI/SacI-digested): 2.8-kbp KpnI/SacI fragment (diamond).

Lane 2: λgt11 without insert (KpnI/SacI-digested): 2.08-kbp KpnI/SacI fragment (diamond)

Lane 3: λgt11 DNA with insert (SacI/Eco RI-digested): 1.06-kbp SacI/Eco RI fragment (double diamond)

Lane 4: λgt11 DNA without insert (SacI/Eco RI-digested): 1.8-kbp SacI/Eco RI fragment (double diamond)

Lane 5: λ.wild type DNA PstI-digested.

Figure 4A:
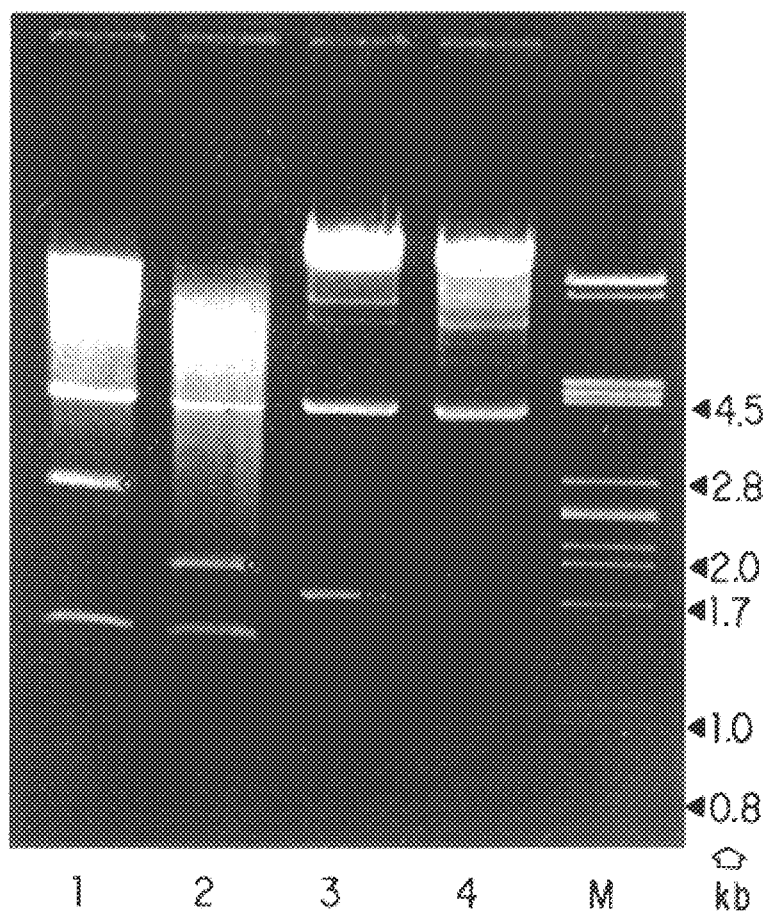
Figure 4B:
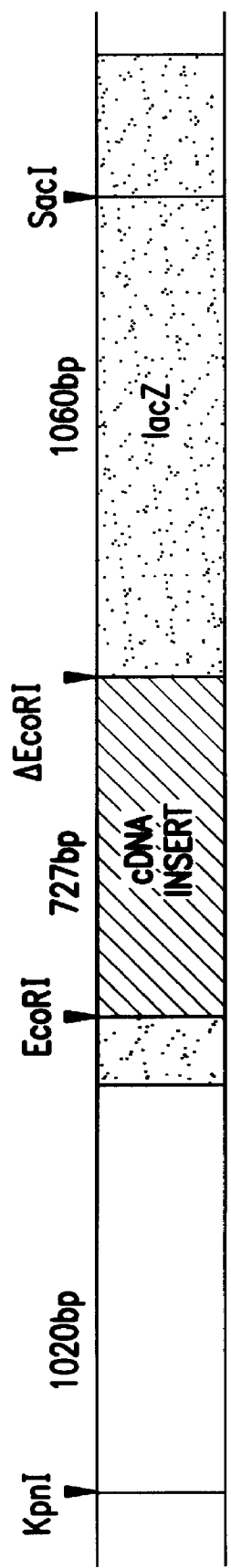

FIG. 4B. Segment of λgt11 genome with CDNA insert, the two Eco RI cleavage sites (the one situated proximal to the SacI site is deleted) and the flanking KpnI and SacI cleavage sites. The lac Z gene region is shaded.

Figure 5A:
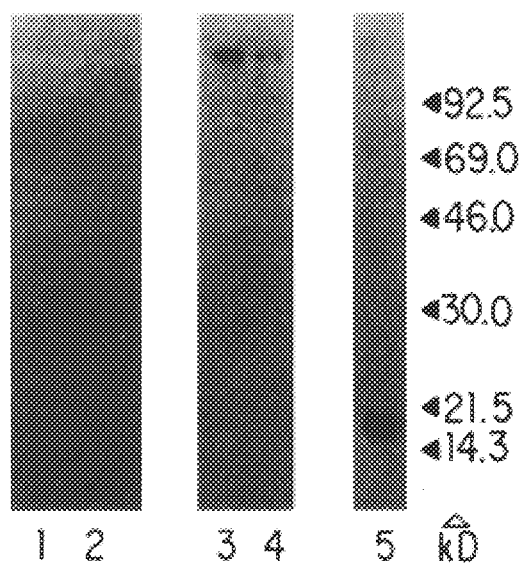
Figure 5B:
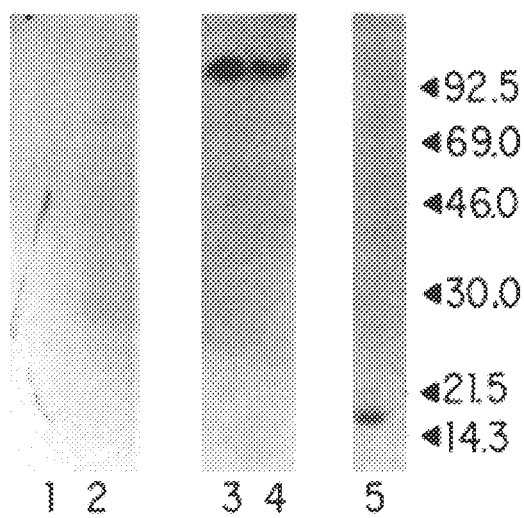

FIG. 5A–5B. Western Immunoblot

FIG. 5A. Immunoblot with serum from allergic subject; detection with $^{125}$I-anti IgE.

Lane 1: Protein extract from *E. coli* Y 1089

Lane 2: Protein extract from *E. coli* Y 1089 infected with λgt11, without insert Lane 3: Protein extract from *E. coli* Y 1089 infected with λgt11, insert-bearing (clone HB6)

Lane 4: Protein extract from *E. coli* Y 1089 infected with λgt11, insert-bearing (clone HB8)

Lane 5: Birch pollen extract BP VIII D

FIG. 5B. Immunoblot with monoclonal antibodies BIP 1: Detection with anti-mouse IgG (rabbit) and $^{125}$I-anti-rabbit Ig.

Lane 1: Protein extract from *E. coli* Y 1089

Lane 2: Protein extract from *E. coli* Y 1089 infected with λgt11, without insert Lane 3: Protein extract from *E. coli* Y 1089 infected with λgt11, insert-bearing (clone HB6)

Lane 4: Protein extract from *E. coli* Y 1089 infected with λgt11, insert-bearing (clone HB8)

Lane 5: Birch pollen extract BP VIII D

Figure 6:
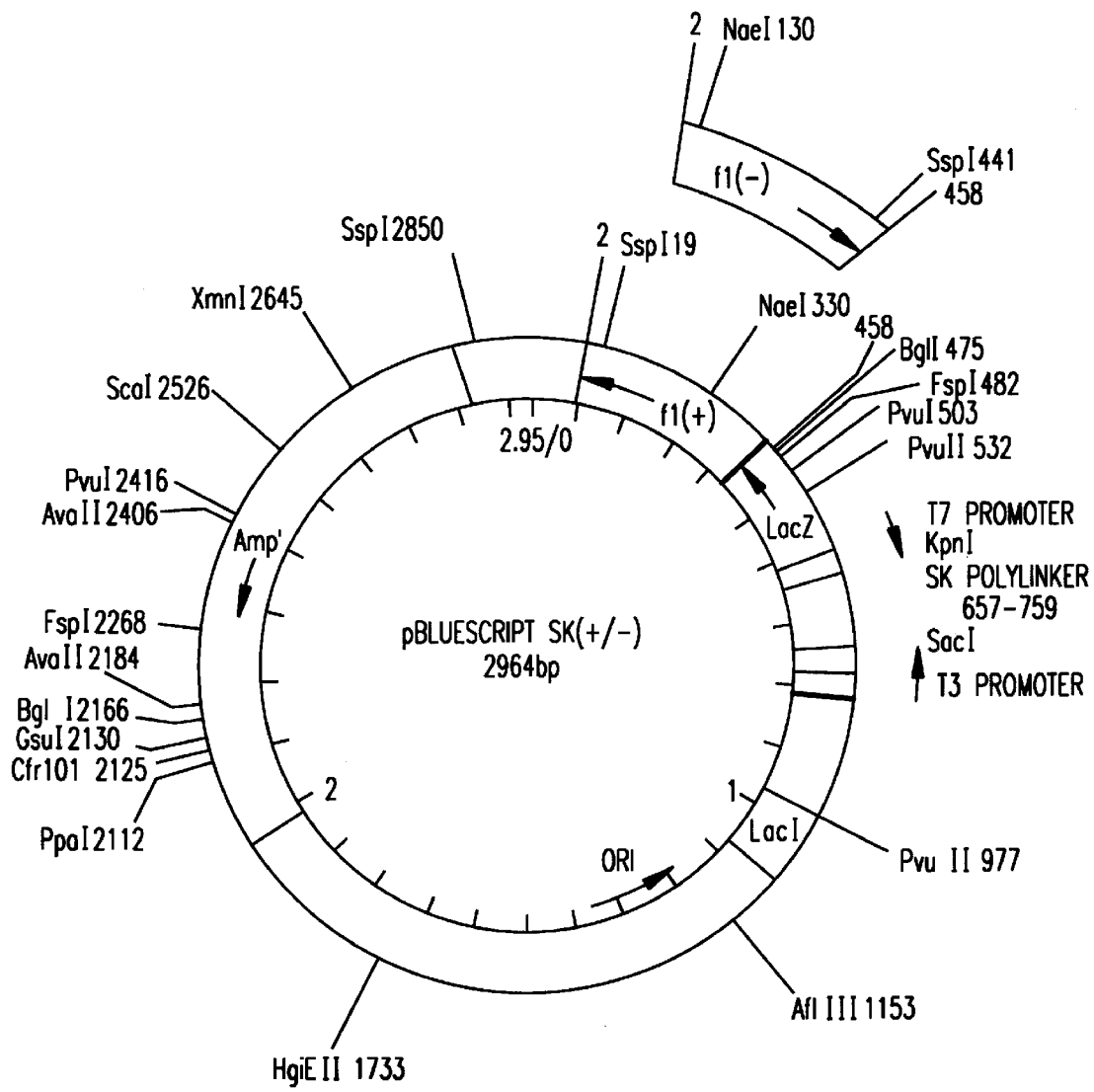

FIG. 6. Restriction map of the plasmid pBluescript SK(+/−).

Figure 7:
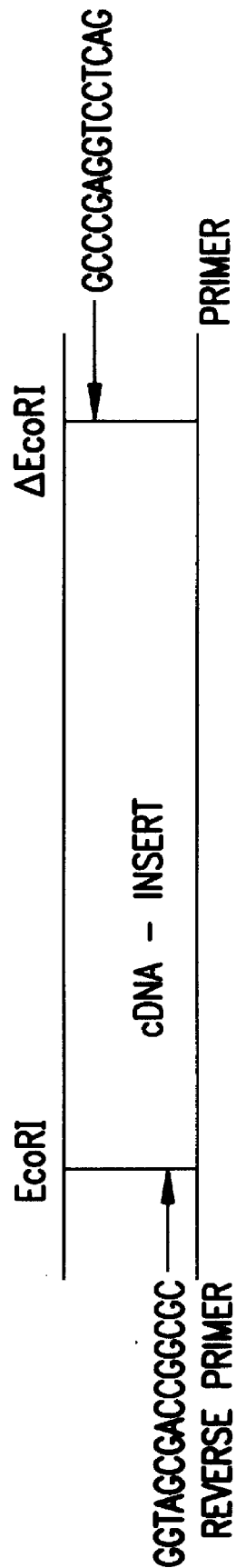

FIG. 7. Segment of the 2.8-kb fragment to illustrate the cDNA insert with λgt11 sequencing primer; the arrows show the direction of synthesis.

Figure 8:
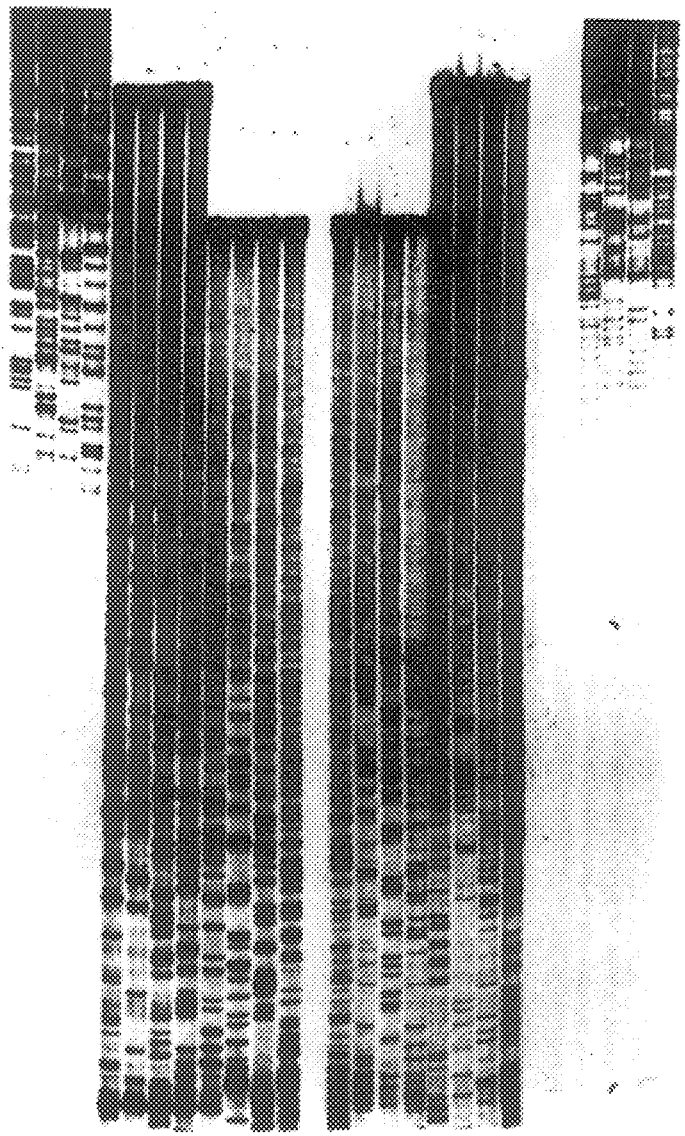

FIG. 8. Autoradiograph of the sequencing gel after the first sequencing of the CDNA insert with the help of λgt11 primer and sequenase; radioactive isotope: $^{32}$p.

Figure 9:
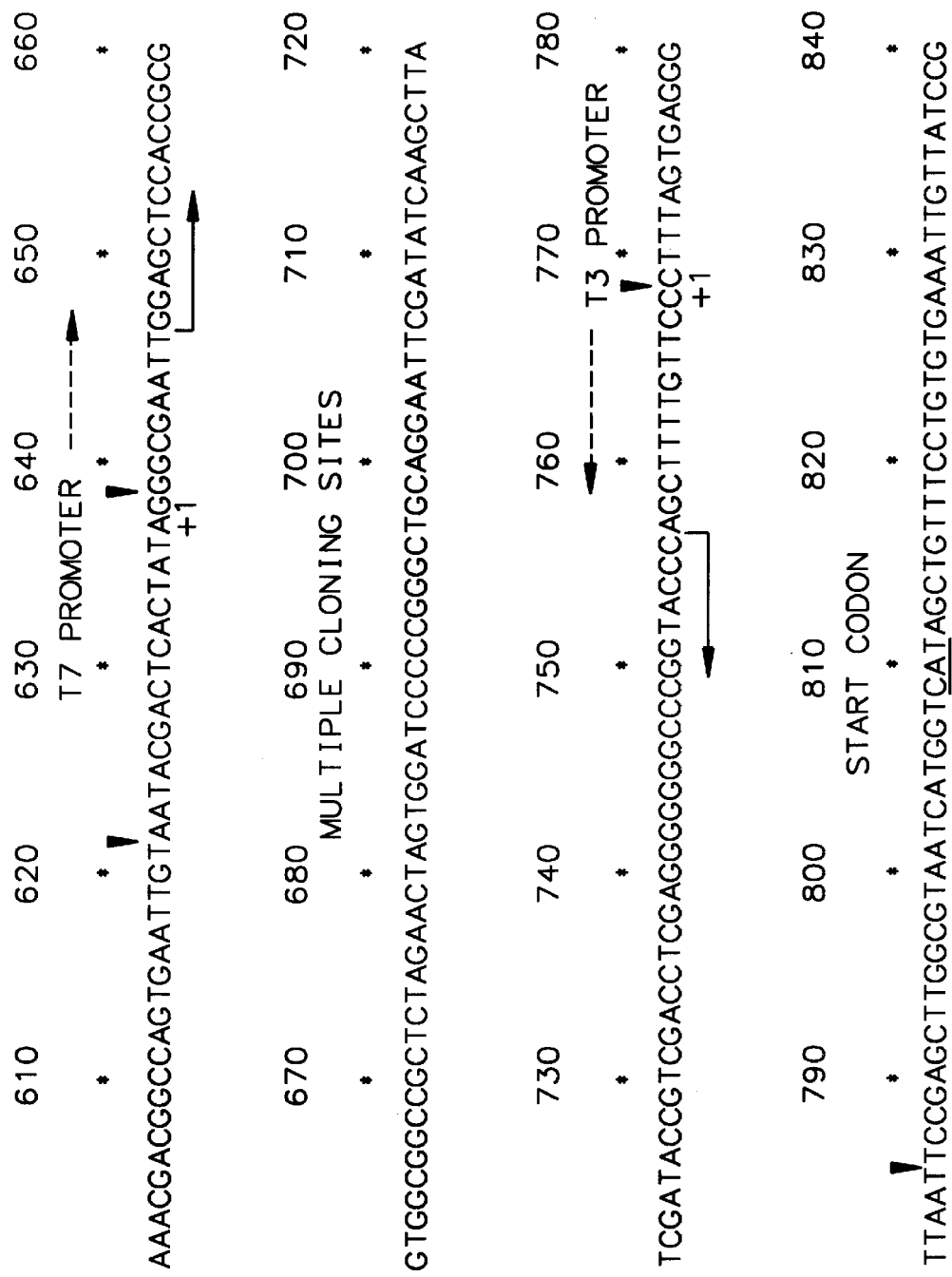

FIG. 9. Segment of the lac Z gene of the Bluescript plasmid. The sequence shows the area from the T7 promoter to the T3 promoter. Between them is the polylinker. The beginnings and ends of both primers are indicated by arrows.

FIGS. 10A–10B. The definitive sequence of the cDNA insert of the principal allergen of the birch Bet v I.

6. EXAMPLE
6.1. ISOLATION OF RNA

RNA isolation was carried out in:

(1) Leaves;

(2) Inflorescences, roots and callus tissue;

(3) Pollen of Betula verrucosa.

6.1.1. LEAF RNA EXTRACTION

Five grams of leaf material, kept at minus 70° C. or freshly picked and transported in liquid $N_2$, was ground to dust in a mill cooled with $N_2$. The dust was transferred to a mortar and the following solutions were added:

(1) 8 ml Tris(hydroxymethyl)-aminomethane/sodium-dodecyl sulfate (Tris/SDS) buffer (0.1M Tris.HCl pH 8.0, 1% w/v SDS);

(2) 4 ml with 1M Tris.HCl, pH 8.0, buffered phenol;

(3) 4 ml $CHCl_3$/isoamyl alcohol (24:1, CI).

The pulverized tissue was stirred to a fine suspension in this mixture (1)–(3), transferred to Corex tubes, vigorously mixed and centrifuged in a Sorvall centrifuge for 5 minutes at: 6800 g and 4° C. A repeated PCI (phenol-$CHCl_3$-isoamyl alcohol) extraction of the aqueous phase, a phase separation by centrifugation at 3000 g for 5 minutes and repeated $CHCl_3$ extraction of the aqueous phase were carried out. 10% by volume 2M $CH_3COONa$ (NaAc) pH 5.8 and 250% by volume absolute ethanol (EtOH) were added to this and the total nucleic acids were precipitated overnight at minus 20° C.

The latter were centrifuged off at 3000 g and 4° C. for 10 minutes in a Beckmann JS13-1 "swing out" rotor, the supernatant was discarded and the pellet was washed with 70% EtOH and dried in a desiccator. The pellet was then dissolved in 2 ml $H_2O$ and transferred to Eppendorf reaction tubes. This was followed by the addition of 150 mg solid NaCl/ml and storage of the solution at 4° C. for 5 hours.

The RNA precipitated after this period was pelleted in an Eppendorf centrifuge at 4° C. and 15,000 g. The pellet was washed with 0.5ml 2.5M NaCl, the RNA again pelleted as above and the washing operation repeated. The pellet was then washed three times with 0.5ml 70% EtOH, dried and dissolved in 360 μl sterile water. Precipitation of the RNA was effected by the addition of 40 μl 2M NaAc, pH 5.8 and 1 ml absolute EtOH at −20° C. overnight. The RNA was again pelleted, the pellet washed twice with 0.5 ml 70% EtOH, dried and dissolved in 100 μl sterile water. The RNA was stored at minus 20° C.

6.1.2. INFLORESCENCES, ROOT MATERIAL AND CALLUS TISSUE RNA EXTRACTION: CETYLTRIM-ETHYLAMMONIUM BROMIDE (CTAB) METHOD

Thirty grams of plant material were pulverized in liquid $N_2$ and an equal volume of boiling extraction buffer (2% CTAB, 100 mM tris HCl at pH 7.8, 20 mM EDTA, 1.4M NaCl, 1% β-mercaptoethanol) was poured over it. The temperature of the solution was brought to 50° C. in a water bath with stirring and the mixture was transferred to SS-34 centrifuging tubes, diluted with an equal volume of $CHCl_3$:isoamyl alcohol (24:1, CI) and carefully mixed. Centrifuging was done for 10 minutes at 17,400 g in a Sorvall SS-34 centrifuge at room temperature. The aqueous phase was transferred to a second tube and a one-tenth volume of 10% CTAB solution was added (10% CTAB, 0.7M NaCl). This was followed by a further CI extraction. To the drawn-off aqueous phase there was added an equal volume of precipitation buffer (1% CTAB, 50 mM Tris, 10 mM EDTA at pH 8.0) and the solution was thoroughly mixed. The solution was allowed to stand for 30 minutes at room temperature, then the nucleic acids were centrifuged off in an SS-34 rotor for 5 minutes at 3000 g. The pellet was dissolved in 10 ml of a 1M buffered CsCl solution (50 mM Tris, 5 mM EDTA, 50 mM NaCl at pH 8.0). Centrifuging was done over a cushion made of 5.7M buffered CsCl (2 ml, 50 mM Tris, 5 mM EDTA, 50 mM NaCl at pH 8.0) for 18 to 20 hours at 120,000 g in a "swing out" rotor. The RNA was contained in the pellet; it was dissolved in sterile $H_2O$, precipitated and stored at minus 20° C.

6.1.3. RNA ISOLATION FROM POLLEN

Five hundred milligrams of pollen were ground in a mortar with fine powdered glass and liquid $N_2$. This was followed by the immediate addition of 20 ml PCI, 10 ml homogenization buffer (10 mM Tris, 200 mM NaCl, 5 mM $MgCl_2$ at pH 9.0) and 0.5 ml 20% SDS. Grinding continued uninterrupted until the initially frozen mixture was liquefied. This mixture was then transferred to an SS-34 centrifuging tube and placed on ice. The mortar was washed out with 5 ml of homogenization buffer and 1% SDS. The solution was vigorously mixed for 10 minutes in centrifuging tubes with constant cooling in ice and then centrifuged for 10 minutes at 3000 g and 4° C. This was followed by two PCI extractions and one CI extraction of the aqueous phase. Precipitation of the nucleic acids was done overnight at −20° C. by adding 10% by volume of 3M NaAc at pH 4.8, and 250% by volume absolute EtOH. After 10 minutes of centrifuging at 12,000 g and 4° C. the pellet was washed once with 70% EtOH, without being detached from the wall of the centrifuging tube, and dissolved in a small quantity of $H_2O$ and divided among Eppendorf reaction tubes. A further precipitation was done by adding 10% by volume of 3M NaAc at pH 4.8, and 250% by volume of absolute EtOH.

6.1.4. CONCENTRATION OF RNA

Concentration of poly(A)$^+$RNA was effected in all cases (Sections 6.1.1–6.1.3) in accordance with the following method.

The precipitated RNA was pelleted by centrifugation for 10 minutes in an Eppendorf centrifuge at 15,000 g and 4° C. The pellet was dried in a desiccator for 10 minutes and then resuspended in 300 μl of sterile $H_2O$ on ice.

Oligo(dT)-cellulose was thoroughly suspended in 0.1M KOH. This suspension was poured into a plastic column having a capacity of 1 ml and stoppered with quartz wool, and the column was filled ¾full. Next the column was washed with 5 ml of 0.1M KOH and rinsed with water until a neutral pH value was obtained. The column was equilibrated with 4 ml of loading buffer (0.5M LiCl, 10 mM Tris.HCl at pH 7.5, 1 mM EDTA, 0.1% SDS).

The RNA probe was adjusted with a 5M LiCl solution to a 0.5M LiCl concentration, denatured for 10 minutes at 60° C. and then quickly cooled over dry ice. The probe was applied to the column, subsequently washed with 1 ml of loading buffer and again applied to the column. Thereafter the column was rinsed with 5 ml of "middle rinse" buffer (10 mM Tris.HCl at pH 7.5, 1 mM EDTA, 0.15 mM LiCl, 0.1% SDS).

The elution of the poly(A)$^+$RNA-containing fraction was effected by rinsing the column with 8×300 $\mu$l portions of elution buffer (2 mM EDTA at pH 8.0, 0.1% SDS) heated to 60° C. The RNA was precipitated at −20° C. overnight at a concentration of 0.3M by the addition of 3M NaAc at pH 4.8, and 300% by volume of absolute EtOH.

6.2. RNA CHARACTERIZATION

RNA characterization was effected by:
(a) Applying the total RNA to a polyacrylamide (6%)-urea (50%) gel and electrophoresis with the use of 5S, 16S and 23S RNAs as reference substances (FIG. 1);
(b) Determination of the poly(A)$^+$RNA-containing fraction by oligo(dT)-column was effected by applying aliquots to 1% agarose plates with 0.5 $\mu$g ethidium bromide/ml and visualizing the dots on a UV transilluminator.

6.3. DNA SYNTHESIS

One microgram of poly(A)$^+$RNA was used for CDNA synthesis in the following reaction.
(a) Synthesis of the first strand:
4 $\mu$l 5× buffer for the synthesis of the first strand (250 mM Tris.HCl at pH 8.3, 250 mM KCl, 50 mM MgCl$_2$, 50 mM dithiothreitol);
1 $\mu$l 20 mM sodium pyrophosphate;
1 $\mu$l human placental RNAse inhibitor (20 U/$\mu$l);
2 $\mu$l deoxynucleotide triphosphate mix (DATP, dGTP, dTTP: 10 mM; dCTP: 5 mM);
1 $\mu$l oligo(dT) (12–18) 1.6 mg/ml;
0.5 $\mu$l $^{32}$P-$\alpha$-dCTP (5 $\mu$Ci);
H$_2$O to 20 $\mu$l.

After mixing, 20 U of reverse transcriptase were added, and this was followed by incubation at 42° C. for 60 minutes. The measurement of synthesis of the first strand yielded a typical incorporation of 100,000 cpm/$\mu$g RNA.

(b) Synthesis of the second strand:
20 $\mu$l of reaction mixture from (a);
20 $\mu$l 5× buffer for the synthesis of the second strand (100 mM Tris.HCl at pH 7.5, 0.5M KCl, 25 mM MgCl$_2$, 50 mM (NH$_4$)$_2$SO$_4$, 50 mM dithiothreitol);
5 $\mu$l $^{32}$P-$\alpha$-dCTP (50 $\mu$Ci);
0.8 U ribonuclease H from E. coli;
23 U DNA polymerase I from E. coli;
H$_2$O to 100 $\mu$l.

Mixing and incubating: 12° C. for 60 minutes, 22° C. for 60 minutes, and then 70° C. for 10 minutes. This was followed by cooling of the reaction mixture on ice, addition of 2.0 U T4 DNA polymerase and incubation at 37° C. for 10 minutes (here, as before, it was possible to take an aliquot for the measurement of radioactive incorporation into the second strand; this yielded an incorporation of 90% of the incorporation into the first strand).

Subsequently the double-stranded cDNA was extracted twice with PCI and once with CI. It was precipitated with the same volume of 4M NH$_4$ acetate and 200% by volume of absolute EtOH for 20 minutes at −70° C. The cDNA was centrifuged for 10 minutes at 15,000 g and 4° C.; the pellet was dissolved in 100 $\mu$l of sterile H$_2$O and then precipitated again, as specified above. The pellet, after being centrifuged again, was washed with 500 $\mu$l of 70% EtOH, centrifuged for 5 minutes as before, and dissolved in 20 $\mu$l of sterile H$_2$O.

6.4. cDNA CLONING IN $\lambda$gt11

6.4.1. METHYLATION OF cDNA

Methylation of cDNA for protection of internal Eco RI restriction sites utilized the following reaction mixture:
1 $\mu$g cDNA in 10 $\mu$l of sterile H$_2$O;
4 $\mu$l 5× Eco RI-methylase buffer (250 mM Tris.HCl at pH 7.5, 5 mM EDTA, 25 mM dithiothreitol);
2 $\mu$l 100 $\mu$M S-adenosyl-L-methionine (stock solution: 10 mM S-adenosyl-L-methionine in 10 mM CH$_3$COONa buffer at pH 5.0, dilution 1:10$^{-2}$ in sterile H$_2$O shortly before use);
4 $\mu$l sterile H$_2$O;
20 U Eco RI methylase. Incubation was at 37° C. for 60 minutes, enzyme activation at 70° C. for 10 minutes.

6.4.2. LIGATION OF ECO RI LINKER

Ligation of the Eco RI linker: 5'd(pGGAATTCC), 500 $\mu$g/ml. Linker ligation:
20 $\mu$l of methylation reaction from Section 6.4.1;
3 $\mu$l 10× ligation buffer (500 mM Tris.HCl at pH 7.5, 100 mM MgCl$_2$, 100 mM dithiothreitol, 50 mM ATP, 50 $\mu$g/ml bovine serum albumin);
1 $\mu$l Eco RI linker (0 5 $\mu$g/$\mu$l);
5 $\mu$l sterile H$_2$O;
5 U T4 DNA-ligase.

Incubation at 15° C. for 16–20 hours. Via the T4 DNA-ligase, the Eco RI linkers were ligated at both ends of cDNA.

6.4.3. DIGESTION OF ECO RI-LINKER cDNA WITH ECO RI

In this way an individual Eco RI "sticky end" was created at each end of the cDNA and surplus linker molecules were removed. The reaction consisted of:
30 $\mu$l of reaction mixture from Section 6.4.2;
10 $\mu$l 10× Eco RI buffer;
60 $\mu$l sterile H$_2$O;
100 U Eco RI (1M Tris.HCl at pH 7.5, 0.5M NaCl, 0.1M MgCl$_2$).

Incubation was at 37° C. for 5 hours, with subsequent enzyme activation at 70° C. for 10 minutes.

6.4.4. SEPARATION OF cDNA FROM SURPLUS LINKER MOLECULES

Prior to the insertion of cDNA in $\lambda$gt11, the excess linker molecules must be detached, so as not to interfere with cloning. For this detachment use was made of commercially obtainable columns which were washed and equilibrated with 6 ml of STE buffer (5.84 g NaCl, 1.21 g Tris, 0.37 g EDTA/l at pH 8.0). One hundred microliters of CDNA digested with Eco RI and linkered were applied to the column. Two hundred microliter portions were eluted from the column with STE buffer and collected separately in Eppendorf reaction tubes. The activity of the individual probes was counted by the Cerenkov method and the fractions with the highest resulting count were pooled. The precipitation of the cDNA of these fractions was effected overnight at −20° C. by the addition of 10% by volume of 3M NaAc and 250% by volume of absolute EtOH. The precipitated cDNA was centrifuged for 30 minutes in an Eppendorf centrifuge at 15,000 g and dissolved in sterile H$_2$O to a concentration of 50 ng/$\mu$l.

6.4.5. INSERTION OF cDNA PROVIDED WITH ECO RI ENDS INTO λgt11

λgt11 DNA was already cut with Eco RI and dephosphorylated with alkaline phosphatase (Clontech RI-λgt11, Cat. No. 6331-1) and was thus ready for the ligation reaction:

200 µg cDNA;

1 µg λgt11 arms;

1 µg 10× ligation buffer (as in Section 6.4.2);

$H_2O$ to 10 µl;

2.5 U T4 DNA ligase.

Incubation was done overnight at 14° C.

6.4.6. IN VITRO PACKAGING

In vitro packaging of the ligation mix was done with Gigapack Plus (Stratagene, Catalog No. 200211).

Regarding the quick thawing of both extracts (Sonic Extract or SE, from the induced prehead donor BHB 2690; Freeze/Thaw Extract or FTE, from the induced packaging protein donor BHB 2688), all the ligation preparation was added to the thawed FTE and 15 µl of SE were pipetted to it and the mixture was carefully mixed with the pipette. Incubation for 2 hours at room temperature followed. After that, 500 µl of phage dilution buffer (500 mg NaCl, 200 mg $MgSO_4$, 5 ml 1M Tris.HCl at pH 7.5) were added. The phage suspension was stored at 4° C.

6.4.7. PREPARATION OF THE E. COLI Y 1090 HOST CELLS

E. coli Y 1090 (ATCC No. 37196, E. coli delta lac.U.169proA$^+$delta lon araD139 strA hflA150 (chr::Tn10) (pMC9)) was spread on an LB-amp plate (1000 ml consisting of 10 g Trypton, 5 g yeast extract, 10 g NaCl, 15 g agar, 100 mg ampicillin at pH 7.5) and incubated overnight at 37° C. Individual colonies were picked and incubated overnight at 37° C. with the addition of 0.4%.maltose. The overnight culture was centrifuged and resuspended in 1 ml of 10 mM $MgSO_4$. These cells were ready for phage adsorption and could be stored at 4° C.

6.4.8. TITRATION OF λGT11 RECOMBINANTS

A serial dilution of phage suspensions (after packaging) was prepared in steps of 10. In each case 100 µl of Y 1090 cells in 10 mM $MgSO_4$ were mixed with 10 µl of phage suspension of the corresponding dilution. Preadsorption of the phage particles onto the host cells took place for 20 minutes at room temperature. Thereafter, the following were added:

2 µl of ampicillin (25 mg/ml); 10 µl of 100 mM IPTG (isopropyl-β-D-thiogalactopyrosanide dissolved in sterile $H_2O$ );

10 µl of a 2% X-gal solution (20 mg 5-bromo-4-chloro-3-indolyl-β-D-galactopyranoside in 1 ml dimethylformamide) per ml;

4 ml of 0.6% agarose in $H_2O$ (kept at 47° C. in a water bath).

The top agarose was quickly mixed and poured onto preheated (37° C.) LB-amp plates. The plates were allowed to stand at room temperature for 10 minutes in order for the top agarose to solidify and then incubated overnight at 43° C. On the following day the white plaques, and hence the recombinant λgt11 phages, were c ounted.

6.5. EXPRESSION OF RECOMBINANT PROTEINS AND IMMUNOSCREENING

The λgt11 vector permits the controlled expression of the recombinant protein in the form of a fusion protein with β-galactosidase.

6.5.1. PLATING THE cDNA BANK

Y 1090 host cells were prepared in the manner described above, infected with phages and plated on LB-amp plates (diameter: 145 mm) in such a way that a density of 20,000 plaques per plate was achieved. The plates were incubated for 3–4 hours at 43° C., until the plaques appeared.

6.5.2. INDUCTION OF PROTEIN EXPRESSION

The plates with the plaques were overlaid with nitrocellulose filters (diameter: 132 mm), soaked in 10 mnM IPTG and then dried and incubated at 37° C. for 3 hours (induction of expression). Thereafter the nitrocellulose membranes, to which the fusion proteins had also been adsorbed, were carefully removed.

6.5.3. IMMUNOSCREENING

6.5.3.1. SCREENING WITH IgE FROM PATIENTS

Washing out agarose particles: the nitrocellulose filter was coated over with 50 ml of GP (50 mM sodium phosphate buffer at pH 7.5, 0.5% Tween 20, 0.5% w/v bovine serum albumin 0.05% $NaN_3$) and shaken on a rotary shaker for 5 minutes at 200 rpm. The buffer was poured off and the process was repeated.

Saturation of the free binding sites was effected with 25 ml GP for at least 30 minutes at room temperature, with gentle shaking.

The selected serum, "llst antibodies", of an allergic subject whose IgE antibodies recognized the main allergen of the birch (Bet v I), a 17.5 kD protein, was diluted 1:10 in GP; with this serum dilution the blots were incubated overnight at 4° C. with gentle shaking.

The blots were carefully washed three times, each time with 30 ml GP at room temperature, the blots being shaken with the buffer for at least 30 minutes during the last of these washing processes. After this the buffer was poured off.

For each round filter, 26 ml of a solution of radioactive "2nd antibodies" was applied, which consisted of:

2.6 ml $^{125}$I-labeled anti-human IgE (Pharmacia Int., 300,000 cpm/ml);

23.4 ml GP (see above);

234 µl gelatine (100 µl/10 ml GP).

Incubation took place overnight at room temperature, with gentle shaking.

The blots were washed three times, each time with 30 ml of GP, the buffer solution being shaken over the blots for 30 minutes during the last of these washing processes.

After the blots were dried, the λgt11 clones with the insert coding for Bet v I were detected autoradiographically by exposure with a Kodak XR Roentgen film for 72 hours at −70° C.

6.5.3.2. SCREENING WITH THE MONOCLONAL ANTIBODY BIP 1

The blots were washed with 50 ml TBS (50 mM Tris.HCl at pH 7.4, 150 mM NaCl, 0.5% Tween 20) for 5 minutes at 200 rpm on a rotary shaker at room temperature. Then the buffer was poured off and the process was repeated once.

Saturation of the free binding sites was done with 25 ml TBS/PM (3% w/v dry powdered milk in TBS) for at least 30 minutes at room temperature and at 200 rpm. 25 ml of undiluted BIP 1 hybridoma culture supernatant ("1st antibodies") per nitrocellulose filter were used; incubation took place overnight at 4° C., with gentle shaking.

The blots were washed three times at room temperature, each time with 30 ml pure TBS, the blots being shaken at room temperature for at least 30 minutes during the last of these washing processes.

The blots were incubated for an hour at room temperature with a rabbit anti-mouse-IgG antibody ("2nd antibodies", Jackson, Inc., Md., USA; affinity purified, diluted 1:2000 in TBS/PM), with gentle shaking.

Washing was done three times with TBS at room temperature, the last washing process being for 30 minutes with gentle shaking. "3rd antibody" incubation utilized:

26 ml per nitrocellulose filter;

26 ml TBS/PM;

13 μl of $^{125}$I-labeled anti-rabbit Ig from goats (Kirkegaard & Perry Labs., London, GB, 300,000 cpm/ml).

Incubation took place for 1 hour at room temperature, with gentle shaking.

Washing was done four times, each time with 30 ml TBS (final washing process was for 30 minutes at room temperature and at 200 rpm on the rotary shaker). The blots were dried and exposed for 72 hours as described above.

Optic detection of the positive clones whose fusion protein was capable of binding human IgE (FIG. 2) or the monoclonal antibody BIP 1 was done by means of the darkening on the X-ray films.

6.6. RECLONING AND ANALYSIS OF RECOMBINANT λgt11 PHAGES AT THE DNA LEVEL

6.6.1. RECLONING

Because of the high density of the plaques, two recloning steps had to be carried out in order to concentrate the positive clones. Phage punches of the positive plaques were prepared, and from them phage suspensions were made. These were again titrated for phage concentration. The positive clones were determined afresh with the help of immuno-screening. It was possible to achieve a concentration of up to 95% (FIG. 2).

6.6.2. DNA ANALYSIS

6.6.2.1. PRODUCTION OF A LIQUID LYSATE

A singular plaque was "soaked" in 500 μl of 10 mM MgSO$_4$ for at least two hours at 4° C. One hundred microliters of this phage eluate was mixed with 100 μl of E. coli Y 1090 cells in 10 mM MgSO$_4$ and allowed to stand at room temperature for 20 minutes for adsorption of the phages by the host cells. This mixture was transferred to 50 ml of LB medium. The bacterial cells were allowed to grow at 32° C. to an adsorbance at 600 of 0.5–0.6. Then the temperature of the cell culture in the water bath was quickly brought to 42° C. and maintained at 42° C. for an additional 20 minutes in an air-bath shaker. After that, the culture was incubated at 37° C. until the lysis of the bacterial cells was completed. Any bacterial cells that were still intact were lysed by the addition of 10 μl of CHCl$_3$. The lysate was centrifuged off for 10 minutes at 10,0000 rpm in an SS-34 rotor. The supernatant containing the phage particles could be stored at 4° C.

To the 50 μl of phage lysate, 10 μl of DNase (5 mg/ml) and 25 μl of RNAse (10 mg/ml) were added and the resulting mixture was incubated for an hour at 37° C. The phages were next pelleted for 1.5 hours at 30,000 rpm in a Beckmann SW-27 rotor. The pellet was resuspended in 200 μl of 50 mM Tris.HCl at pH 8.0. Phenol extraction was done by adding an equal volume of buffered phenol. The suspension had to be vigorously shaken for 20 minutes and then centrifuged for 2 minutes.

Phenol extraction had to be repeated. To the aqueous phase, 200 μl of CHCl$_3$ were added and thoroughly mixed and the mixture was centrifuged for a short time. This process, too, had to be repeated. The phage DNA was precipitated at room temperature by the addition of 20 μl of 3M NaAc and 600% by volume of absolute EtOH to the aqueous phase. After 10 minutes of centrifuging the pellet was washed with 1 ml of 70% EtOH, then dried and resuspended in 200 μl of sterile H$_2$O.

6.6.2.2. RESTRICTION ANALYSIS

One microgram of λgt11 DNA was digested with Eco RI. Due to the fact that the insert could not be cut out from the vector, the two restriction recognition sites located next to the insertion site had to be chosen: KpnI and SacI (see λgt11 restriction map, FIG. 3). In this way it was possible to cut out from the vector a 2.8 kb DNA fragment (FIG. 4A; lane 1; FIG. 4B) that in addition to the insert contained 1000 bp of original λ sequence, both to the right and to the left (FIG. 4B). Double digestion with KpnI/Eco RI or SacI/Eco RI showed that in fact only one of the two Eco RI recognition sequences had been changed, the one located closer to the site of the SacI cut. In this way an Eco RI—SacI fragment measuring 1.75 kbp was obtained (FIG. 4A; lane 3, marked with a double diamond). For subcloning in the Bluescript plasmid the 2.8 kb) KpnI-SacI fragment was used (FIG. 4A, lane 1, marked with a single diamond).

6.7. FUSION PROTEIN AND WESTERN BLOT

The following methods were used to demonstrate the biological activity (IgE-binding capacity) of the fusion protein produced in λgt11

6.7.1. PRODUCTION OF E. COLI Y 1089 LYSOGENS

Individual colonies of Y 1089 (ATCC No. 37196; E. coli delta lac U169 proA$^+$delta ion araD139 strA hflA 150 (chr::Tn10) (pMC9)) were inoculated with 0.4% maltose in 10 ml of LB-amp medium and allowed to grow overnight at 37° C. One milliliter of this overnight culture was transferred into 50 ml of LB-amp—maltose medium preheated to 37° C. and brought up to an absorbance at 600 nm of 0.5. Next, 1% by volume of 1M MgSO$_4$ was added to the culture, which was then divided into 100 μl portions. To these, 50 μl of a phage dilution (1.25×10$^8$ plaque-forming units/ml) were pipetted. Adsorption of phages on the Y 1089 cells took place for 20 minutes at room temperature. The E. coli cells thus infected were spread out on LB-amp plates in a thickness of approximately 5 cells/cm$^2$. The plates were incubated overnight at 32° C. Individual colonies were picked and smeared on two separate LB-amp plates. One plate was incubated at 32° C., and one at 43° C. Lysogenic Y 1089 cells grew at 32° C., but not at 43° C.

6.7.2. PRODUCTION OF A PROTEIN EXTRACT FROM LYSOGENIC CELLS

One hundred milliliters of LB medium were inoculated with an individual colony of a recombinant lysogenic E. coli Y 1089. The culture was allowed to grow to an absorbance at 600of 0.5, and then the temperature was quickly raised to 42° C. The culture was kept at 42° C. for 20 minutes. The addition of IPTG at a concentration of 10 mM led to the expression of the fusion protein. The culture was incubated for 60 minutes at 37° C. and the cells were subsequently harvested at room temperature. The cell pellet was resuspended in 1/30of the original culture volume in phosphate buffer (50 mM sodium phosphate buffer at pH 7.5) and immediately frozen in liquid N$_2$. Thawing in a 37° C. water bath led to a complete lysis of the induced lysogenic bacterial cells.

6.7.3. POLYACRYLAMIDE GEL ELECTROPHORESIS (PAGE) AND IMMUNOBLOT

The biological activity (IgE-binding) of the fusion protein was ascertained by Western blot/immunoblot (FIGS. 5A,–5B). By means of SDS-PAGE (12% homogeneous polyacrylamide gel, 5% stacking gel), fractionated proteins (500 μg of total protein extract from recombinant lysogenic E. coli cells per lane) were transferred onto a nitrocellulose filter in the electrical field at 150 mA for 4 hours (transfer buffer: 25 mM Tris.HCl, 192 mM glycine, 20% methanol at pH 8.3). The nitrocellulose was cut into strips, and free binding sites were saturated for 30 minutes at room temperature with the following buffer: 50 mM sodium phosphate at pH 7.5, 0.5% Tween 20, 0.5% BSA, 0.05% NaN$_3$.

The nitrocellulose support was coated over with serum from an allergic subject that was diluted in the buffer used for saturating the free binding sites. For the determination of allergen-specific IgE, the serum of the allergic subject was diluted 1:4 in this buffer; for the determination of the allergen-specific monoclonal antibody (BIP 1), tissue-culture supernatants of hybridoma cells were used undiluted.

The nitrocellulose strips were in each case incubated with the diluted serum or undiluted supernatant overnight at 4° C. in swinging motion. The strips thus incubated were then washed three times in the buffer used for the saturation of the free binding sites. For the determination of the allergen-specific IgE, the strips were incubated for 12 hours at room temperature with $^{125}$I-anti-human-IgE. This anti-IgE was diluted 1:4 in the buffer specified above, which was additionally 20 mM in sodium azide and contained 0.4% gelatine.

For the detection of monoclonal antibody BIP 1, the corresponding antiglobulin reagents (anti-mouse-IgG from rabbits) diluted 1:3000 in the above-specified buffer were added. The incubation time was 1 hour at room temperature, and this was followed by three washings in saturation buffer. Next the nitrocellulose strips were dried and adhered to paper. The quantity of bound $^{125}$I-labeled antibodies was determined by placing the strips in a Kodak cassette with an intensifying sheet with an X-ray film (Amersham RPN 6).

Exposure was at -70° C. for 76 hours. Development was done with commercially obtainable developers for X-ray films. The protein bands marked by the radioactive antibodies were visible due to the corresponding darkening of the film (FIG. 5A,-5B).

6.8. SUBCLONING OF THE 2.8 kb FRAGMENT SacI-KpnI

In the subsequent stage, the cleavage sites near the two Eco RI cleavage sites, namely SacI and KpnI, were selected for electrophoretic isolation of the insertion fragment. The distances between insert-end (Eco RI) and the two restriction sites Sacd and KpnI are 1020 base pairs on the KpnI side and 1060 base pairs on the SacI side (see FIG. 4B).

15 6.8.1. ISOLATION OF DNA FRAGMENT FROM AGAROSE GEL

6.8.1.1. FRACTIONATION

In two passages, the following digests were fractionated on 1% agarose gels:

20 μg of recombinant λgt11 DNA (plus 2.8 kb insert) in 20 μl H$_2$O;
20 μl 10× buffer ("low salt B": 10 mM Tris at pH 7.5, 10 MM MgCl$_2$, 100 μg/ml BSA);
60 U KpnI;
160 μl H$_2$O; for a total volume of 200 μl.

The mixture was incubated for 3 hours at 37° C. For the immediately following SacI digestion, the NaCl concentration was adjusted to 40 mM by adding 2 μl of 4M NaCl in H$_2$O; this approximately corresponds to the optimal "medium salt buffer" for SacI. To this, 60 U of SacI were added and the digest was incubated for an additional 3 hours at 37° C.

The size of 750 bp for the cDNA insert was determined by the difference between the length of the actual fragment of 2830 base pairs and the length of the KpnI-SacI segment of 2080 base pairs, computed from the λgt11 restriction map. For the precise characterization of the cloned cDNA, the fragment obtained was then ligated into a suitable multi-purpose plasmid, namely Bluescript plasmid (FIG. 6), for the purpose of sequencing circular double-stranded and single-stranded DNA.

6.8.1.2. ELUTION OF THE FRAGMENT

The DNA bands at the 2.8 kb level, which are quite visible under UV light because of their "staining" with ethidium bromide, were applied to DE81 Whatman filters, which were placed, through a slot, in front of the gel fragments on the anode side. The filter pieces were each washed with 2×300 μl of low salt wash buffer (0.2 mM NaCl, 10 mM Tris, 1 mM EDTA at pH 8.0) and then the DNA was eluted out with 2×300 μl high salt elution buffer (same as wash buffer except for 1M NaCl). After two phenol and ether extractions of the aqueous phase, followed by ethanol precipitation overnight at -20° C., the DNA was pelleted (15,000 g for 10 minutes) and dried in a vacuum. The total quantity of eluted 2.8 kb fragments of both gels was dissolved in a total of 10 μl of water and combined. An aliquot (0.7 μl) was applied to a 1% agarose gel for quantitative determination. The 2.8 kb bands obtained indicated a total quantity of 200–300 ng for both fragments at a concentration of 20–30 μg/ml. Consequently, ligation in Bluescript was done as a prerequisite for all further characterization steps.

6.8.2. PREPARATION OF PLASMIDS FOR LIGATION

The Bluescript plasmid subvariants M13 SK$^{30}$ and M13 SK$^{31}$ (FIG. 6) were digested with KpnI and SacI. Every 2 μg/2 μl of plasmid (SK$^+$or SK$^-$) were digested with 30 U each of KpnI and SacI (as described in Section 6.8.1.1).

6.8.2.1. LIGATION IN M13 SK$^+$AND M13 SK$^-$

The digested plasmid DNA was washed, pelleted, dried and dissolved in 5 μl H$_2$O (as described in Section 6.8.1.2).

For ligation in the Bluescript plasmid, to every 4.8 μl of eluted and purified 2.8 kb fragment:

5 μl of plasmid (SK$^{+or\ SK-}$);
2 μl DATP (100 mM);
2μl 10 ×ligase buffer (500 mM Tris at pH 7.4, 100 mM MgCl$_2$, 1 10 mM spermidine);
0.5 μl T4 DNA ligase (5 U/μl);
and 6 μl H$_2$O were pipetted and the ligation preparation was incubated for 3 hours at room temperature.

6.8.2.2. PRODUCTION OF COMPETENT CELLS AND TRANSFORMATION

The microorganism selected for transformation was an *E. coli* strain suitable for the Bluescript plasmid, XLI-Blue (recAI, endAI, gyrA96, thi, hsdR17 (rk$^{31}$ mk$^+$) supE44, relaI, λ--, lac-, (F'proAB, lac IgZ delM15, Tn10), which makes possible a selection of insert-bearing Bluescript plasmids by means of the β-galactosidase-blue-white dolor-indicator system (see Section 6.4.8).

*E. coli* XLI-Blue was made "competent" with 100 mM CaCl$_2$ at 0° C. 50 ml of an exponential culture (XLI Blue in LB-tet (tetracycline: 20 mg/l)) were pelleted at an absorbance at 460 at 600 nm. The *E. coli* pellet was first suspended in 50 ml of ice-cold 100 mM CaCl$_2$, centrifuged after a further incubation (20 minutes at 0° C.) and resuspended in 5 ml of 100 mM CaCl$_2$. Transformation was carried out after 4 hours at 0° C.

A fraction (⅕) of each of the two ligase preparations described under Section 6.8.2.1 was incubated with 100 μl of competent XLI Blue cells, and the remainder (⅘) was incubated with 200 μl of competent cells, both at 0° C. for one hour. As a result of a subsequent 2 minute heat shock of the *E. coli* bacteria at 42° C. the plasmid DNA was taken up through the bacterial wall.

After plating of the transformation mixture on LB-tet plates and incubation for 18–24 hours at 37° C., a series of white colonies consisting of SK$^+$and SK$^-$transformants were put into preculture. In a plasmid mini-prep in accordance with the alkaline lysis method, the plasmid DNA was isolated from these precultures and then the presence of the 2.8 kb insert was verified by KpnI/SacI control digestion. Two positive clones, one SK$^+$and one SK$^-$variant (2.8 SK$^+$or 2.8 SK$^-$), were selected for making a large-scale plasmid preparation.

6.8.2.3. LARGE-SCALE PLASMID PREPARATION OF 2.8 SK+ AND 2.8 SK−

The plasmid preparation in accordance with the alkaline lysis method was made from 300 ml of LB medium seeded with XLI-Blue transformants. Separation of plasmid DNA from RNA was done by differential polyethylene glycol (PEG) precipitation followed by phenol ether extraction and isopropanol precipitation.

6.9. SEQUENCING OF 2.8 kb FRAGMENT WITH SEQUENASE

For sequencing, two commercially obtained λgt11 primers were used as a starting point for enzymatic synthesis of complementary strand segments.

1. A 15-base long, single-stranded nucleotide with the sequence:

5'... G A C T C C T G G A G C C C G ... 3', described by the manufacturer as λgt11 primer, which is complementary to a region 12 bases away from the Eco RI insertion site on the λgt11 arm turned toward the SacI cleavage site (FIG. 7).

2. A 15-base long, single-stranded nucleotide with the sequence:

5'... G G T A G C C A C C G G C G C ... 3', described as λgt11 reverse primer, which is complementary to a region 7 bases away from the Eco RI cleavage site on the λgt11 arm turned toward the KpnI cleavage site (FIG. 7).

This provided the possibility of sequencing the insert complementarily from both sides and of thus obtaining the entire nucleotide sequence of the fragment. After being pelleted, washed in 75% ethanol and repelleted, the purified plasmid DNA of 2.8 SK+ and 2.8 SK− was dissolved in 10 μl of water, and an aliquot of 1 μl 1 was applied to a gel for quantitative determination. Based on this, the concentration of DNA was 1.2 μl/μl.

6.9.1. SEQUENCING PROTOCOL
6.9.1.1. ANNEALING REACTION

15 The annealing preparation, total volume 10 μl, consisted of:

2 μl plasmid DNA (1–2 μg/μl);
2 μl H$_2$O;
2 μl 1 sequencing buffer (200 mM Tris at pH 7.5, 100 mM MgCl$_2$, 200 mM NaCl);
1 μl primer (0.67 pMol/μl).

The annealing mixture was taken up in a glass capillary tube which was melted closed on both ends. The tube was processed in boiling water for 5 minutes, quickly dipped in cold (−70° C.) alcohol, left there 5 minutes, then brought to 65° C. and slowly cooled to 35° C. This procedure brings about separation of the double strands and attachment of the primer.

Four annealing preparations were made, two each with primer and reverse primer.

6.9.1.2. LABELING REACTION

For the labeling reaction, the labeling stock solution was diluted 1:2 and 1:10 both for primer sequencing and for reverse primer sequencing. The 1:2 and 1:10 preparations pertain to the relative quantity of deoxy(d)nucleotide in the mixture. The 1:10 dilution was used for short strand pieces for better dissolution of the initial sequences, while the 1:2 dilution was used for longer strand pieces.

Labeling stock solution consisted of:

7.5 μl dGTP;
7.5 μl dCTP; and
7.5 μl dTTP.

For labeling preparation, the four annealing preparations were transferred from the capillary tubes to reaction vessels.

To every 10 μl of annealing mixture were added:

1 μl 0.1M dithiothreitol (DTT);
2 μl deoxynucleotide dilution (1:2 and 1:10 each for primer and reverse primer);
0.5 μl $^{32}$P-α-dATP (1 mCi/ml);
2 μl sequenase (diluted 1:8 in TE).

After thorough mixing, the four preparations were incubated at room temperature for 5 minutes.

6.9.1.3. TERMINATION REACTION

For each preparation four reaction tubes (A, G, C, T), each with 2.5 μl of termination mix (8 μM of each dideoxy(dd) nucleotide), were brought to 37° C. Into each of these, 3.5 pl of the corresponding labeling reaction preparations were pipetted, which results in incorporation of the dideoxy nucleotides, thus ending strand lengthening. After incubation for 5 minutes at 37° C. the reaction was terminated by the addition in each case of 4 μl of a "stop" solution (98.5% formamide, 0.05% bromophenol blue, 0.05% xylene cyanol, 0.5× TE at pH 8). The probes were stored at −20° C. until they were placed on the gel, which was preceded by 2 minute heating of the probes to 75°–85° C. for strand denaturation.

6.9.1.4. SEQUENCING GEL The gel consisted of:

97.5 ml 6% acrylamide (AA) stock solution;
2.5 ml 20× TBE buffer (1M Tris at pH 7.5, 1M borate, 20 mM EDTA);
220 μl 25% ammonium persulfate (APS) solution in H$_2$O;
50μl tetramethylethylenediamine (TEMED).

The 6% AA stock solution contained 57 g acrylamide, 3 g bisacrylamide, and 481 g urea.

Before the gel was poured, the glass plates were cleaned three times with water and three times with alcohol, and one of the plates was scrubbed twice, each time with 5 ml of silanizing solution (2% dichloromethylsilane in chloroform). The gel polymerized overnight at room temperature.

One hour before the application of the probe, the gel was; subjected to 2000 volts in order to create the required temperature for DNA denaturation, i.e., at least 50° C. The probes were heated for 2 minutes to 80° C., and the gel wells were rinsed out thoroughly so as to remove urea "polymerizates". The preparations with the deoxynucleotide labeling mixture diluted 1:2 were each fractionated in two 4-lane runs (AGCT). Between these runs the time interval was from application to the point when the blue marker ran out of the gel, plus an additional hour. After the blue marker flowed out two more times, the 1:10 dilution was applied to four lanes as above and run until the blue marker had reached the lower edge of the gel. Two microliters per well were applied, and the voltage was 1500–2000 volts. After the completion of electrophoresis, the gel was placed on Whatman DEAE paper, dried in a vacuum oven at 80° C. and exposed without intensifying sheet.

6.9.1.5. ANALYSIS OF SEQUENCE DATA

The sequence of the insert as derived from this first sequenase reaction was almost complete as regards length, since the overlapping in the middle section of the insert could be read from both sides (FIG. 8). Based on a restriction analysis of the sequencing data already available, a few important singular 6-base cleavage sites were selected for the purpose of subcloning the corresponding fragments, with subsequent subsequencing. This was necessary due to the fact that the present sequence still exhibited some unclear points, showed contradictions between complementary strand segments, or had nicks in the initial region of both insert ends. The cleavage sites selected were:

1) Bcl I: T G A T C A;

2) Bgl II: A G A T C A;

3) BamH I: G G A T C C.

These three sites exhibit with respect to one another the practical relationship of having the same middle base series "GATC" and, after restriction, form a 4-base overhang. Consequently, fragments cut with these enzymes are ligatable with one another.

6.9.1.6. VERIFICATION OF EXISTING DATA

The correctness of the sequence of the Bgl II and BamH I cleavage site was checked by gel electrophoresis (1% agarose). Both 2.8 SK$^+$ and 2.8 SK$^-$ fragments were digested with the enzyme combinations KpnI/Bgl II, Eco RI/Bgl II and BamH I/Eco RI. The fragments obtained, approximately 1400 bp, 380 bp and 350 bp, respectively, were compatible with the band length computed from the gene map for SK or the 2.8 kb fragment. Deviations of ±30 base pairs were still possible, owing to sequence incompleteness.

The following test procedures were then carried out for the purpose of confirming the sequence data obtained or correcting ambiguities.

6.10. SEQUENCING OF SUBFRAGMENTS OF THE 2.8 FRAGMENT BY THE MAXAM & GILBERT TECHNIQUE

6.10.1. $^{32}$P-LABELING OF SUBFRAGMENTS AFTER Bgl II DIGESTION

The reasoning behind the labeling is that Bgl II digestion gives rise to two 5'-overhanging ends: 5'. . . A..GATCT. . . 3'. These are used by reverse transcriptase (RT) as a starting point for $^{32}$P-α-dATP labeling from 5' to 3'. Subsequent digestion with SacI yields two radioactively tagged fragments:

1) A short Bgl II/SacI fragment of approximately 1400 bp;

2) A long fragment of approximately 4300 bp starting from Bgl II and including the residual plasmid.

For Bgl II digestion of 2.8 SK $^+$, in a total volume of 200 µl, 10 µg DNA were digested overnight at 37° C. with high salt buffer (10 mM Tris at pH 7.5, 10 mM MgCl$_2$, 100 mM NaCl and 100 µg/ml bovine serum albumin) and 60 U Bgl II. The digest was phenolated (¼volume phenol/Tris saturated), extracted twice with ether and precipitated with isopropanol. After pelleting, washing of the pellets in 70% ethanol and repelleting, the DNA was dissolved in 20 µl H$_2$O.

For $^{32}$P-labeling of both Bgl II ends, added in a total volume of 50 µl:

20 µl DNA (1 µg/µl)

5 µl 10× RT buffer;

3 µl $^{32}$P-α-dATP (1 mCi/ml);

5 µl dGTP (10 mM);

1 µl BSA (50 mg/ml);

2 µl RT (20 U/µl);

14 µl H$_2$O.

The mixture was incubated for 1 hour at 25° C.

This was followed by digestion with SacI. In addition, the RT preparation was adjusted to a concentration of 10 mM Tris and 10 mM MgCl$_2$ and thus made "SacI-compatible". The digest was incubated for 1 hour at 37° C.

The elution of both fragments was effected in accordance with the protocol described in Section 6.8.1, from an agarose gel. After phenolation and two ether extractions of the aqueous phase the two eluates were each distributed among five reaction vessels and the labeled fragments were subsequently precipitated with ethanol at −70° C.

6.10.2. SEQUENCING BY THE MAXAM & GILBERT TECHNIQUE

6.10.2.1. SEQUENCING PROTOCOL

The DNA fragments (small fragment: approx. 1400 bp; large fragment: approx. 4300 bp) were washed with 70% ethanol and pelleted (5 pellets/fragment) and sequenced according to the technique of Maxam & Gilbert. After the termination of the sequencing process the pellets obtained from the five preparations (G, G+A, C+T, C, A+C) were individually measured in accordance with the Cerenkov method and then dissolved in different volumes (but each volume was at least 12 µl) of formamide "stop" buffer, so that each mixture displayed the same amount of radioactivity per microliter. The completed probes were stored at −20° C.

6.10.2.2. SEQUENCING GELS

Through application on polyacrylamide (PAA)/urea gels with different AA concentrations (6% or 20%), better resolution was achieved in the initial sequences.

For a 20% gel of 60 ml:

1.5 ml 20× TBE buffer;

58.5 ml 20% AA stock solution;

90 µl 2% APDS (ammonium peroxydisulfate);

40 µl TEMED (N,N,N',N'-tetramethylethylenediamine).

The 20% AA stock contained 197 g AA, 3 g BisAA, and 481 g urea.

Two microliters per lane of each preparation were heated to 80° C. for 2 minutes and then placed on the gels. On the 6% gel the probes, small and big fragments placed next to one another, were fractionated in three 5-lane (G, G+A, C+T, C, C+A) runs at 2000 volts. Both times, the time interval between runs was up to when the blue marker ran out, plus one hour. On the 20% gel only one 5-lane run was fractionated, until the blue marker reached the middle of the gel.

6.10.2.3. EVALUATION OF DATA OBTAINED FROM MAXAM & GILBERT SEQUENCING

By means of this second sequencing run it was possible to fill in the nicks at the insert ends and clear up a large part of the unclear points in the sequence.

6.11. FURTHER SUBCLONING FOR ADDITIONAL CHECKS

6.11.1. ISOLATION OF A BamHI/HincII FRAGMENT WITH SUBCLONING AND SINGLE-STRAND SEQUENCING BY MEANS OF SEQUENASE The object was to describe precisely the change in the non-cleavable Eco RI cleavage sites. For this purpose a singular HincII cleavage site was selected that was situated 126 bases outside of this Eco RI cleavage site on the λgt11 arm turned toward the SacI cleavage site.

For the BamHI/HincII digestion of 2.8 SK$^+$, 3 µg of DNA were digested with 15 U each of BamHI and HincII in high salt buffer (HS). For the same digestion of SK$^+$ and SK$^-$, 2 µl each of SK$^+$ and SK$^-$ were digested by 10 U each of BamHI and HincI in HS buffer. Incubation was done overnight at 37° C.

Following gel electrophoresis, the BamHI/HincII fragment was eluted (see Section 6.8.1.2). Half of the eluate was combined with the SK$^+$ digest, and the other half, with the SK$^-$ digest, and both DNA mixtures were precipitated with ethanol.

After pelleting of both DNA precipitations, ligation and transformation were effected in XLI Blue (as described in Sections 6.8.2.1 and 6.8.2.2).

6.11.2. ISOLATION OF AN Eco RI/Bgl II FRAGMENT WITH SUBCLONING AND SINGLE-STRAND SEQUENCING BY MEANS OF SEQUENASE

For the Eco RI/Bgl II digestion of 2.8 SK+, 12 µg of 2.8 SK+DNA were digested with 60 U each of Eco RI and Bgl II in HS buffer. For the same digestion of SK+and SK−, 2 µg each of SK+and SK−were digested by 10 U of BamHI and 10 U of Bgl II in HS buffer. The incubations were done for 3 hours at 37° C.

The digestions of SK+and SK corresponding to the 2.8 SK+digestion were done with Eco RI and BamHI (the Bluescript plasmid has no Bgl II cleavage site on the polylinker). In this way the ligatability of both palindromic cleavage sites was evaluated.

Following gel electrophoresis the Eco RI/Bgl II fragment was eluted (as in Section 6.8.1.2) and SK+and SK−plasmids digested with Eco RI/BamHI (as described in Section 6.11.1) were precipitated with ethanol.

Ligation and transformation were as described in Sections 6.8.2.1 and 6.8.2.2.

6.11.3. CHECKING TRANSFORMATIONS

The subfragment-bearing SK+and SK−Bluescript plasmids were isolated from the transformants of both ligations by means of plasmid preparation in accordance with the alkaline lysis method.

Control digestions of recombinants consisted of: BamHI/HincII for confirmation of BamHI/HincII insertion; and Eco RI/XbaI for confirmation of Eco RI/Bgl II insertion (because of ligation with the BamHI cleavage site, the BamHI site could no longer be cut).

Both digests were fractionated on agarose gels. In this way the ligation and transformation of both subfragments could be documented in SK+or SK−. At the same time, the starting clone for single-stranded sequencing could be selected in accordance with qualitative and quantitative criteria.

6.11.4. SINGLE-STRANDED SEQUENCING OF BLUESCRIPT DNA SUBFRAGMENTS

6.11.4.1. PRODUCTION OF SINGLE-STRANDED DNA BY HELPER PHAGES

One each of SK+and SK+subclones with the BamHI/HincII fragment or the Eco RI/Bgl II fragment were multiplied in 2.5 ml of preculture (LB/amp/tet) overnight at 37° C. With every 50 µl of this, 2.5 ml of LB were again inoculated. After 30 minutes at 37° C., 10 µl of the Bluescript helper phage R408 with a titer of $5.5 \times 10^{10}$ plaque-forming units/ml were added. to each one and the four cultures were shaken for 8 hours at 37° C. Then 1.2 ml quantities were transferred to reaction tubes and centrifuged for 15 minutes at 15,000 g. The single-stranded variants of the insert-bearing plasmids, i.e.:

Eco RI/BamHI SK+ligated with Eco RI/Bgl II fragment;
Eco RI/BamHI SK−ligated with Eco RI/Bgl II fragment;
HincII/BamHI SK+ligated with HincII/BamHI fragment; and
HincII/BamHI SK−ligated with HincII/BamHI fragment, were now in the supernatant and were precipitated with 300 µl of polyethylene glycol (20% PEG in 3.5M ammonium acetate). After 15 minutes at room temperature, the single-stranded DNA was pelleted and dissolved in 300 µl of TE buffer. After phenol extraction and two ether extractions of the aqueous phase, ethanol precipitation was done by the addition of 50% by volume of 7.5M ammonium acetate at −70° C.

As a primer for single-stranded sequencing with sequenase, two commercial oligonucleotides that corresponded to sections of the Bluescript-LacZ gene on both sides of the polylinker were used:

1. T3 primer, a 17-base long oligonucleotide with the sequence:
   5'...A T T A A C C C T C A C T A A A G...3', added to the polylinker on the SacI side of the SK LacZ gene, for the priming reaction with the SK recombinants (FIG. 9);

2. T7 primer, a 17-base long oligonucleotide with the sequence:
   5'...A A T A C G A C T C A C T A T A G...3', connected before the polylinker on the KpnI side, for the priming reaction with the SK+recombinants (FIG. 9).

6.11.4.2. SEQUENCING PROTOCOL

After PEG treatment, the single-stranded DNAs were washed with 70% ethanol, pelleted and dissolved in 10 µl $H_2O$. After gel control of aliquots (1 µl), every 7.5 µl DNA were introduced into the annealing reaction with approximately 600ng/preparation. The deoxynucleotide dilution for the labeling reaction was prepared with 1.5 (deoxynucleotide stock solution in $H_2O$), and marking was done with $^{32}P$-α-dATP. All the other steps were the same as those already described in the first sequenase sequencing. The termination mixtures were each fractionated in two 4-lane (ACGT) runs, between which was the time interval for the blue marker to run out twice. A 6% gel was used.

6.12. EVALUATION OF THE DATA OBTAINED IN ACCORDANCE WITH THIS THIRD SEQUENCING RUN

The now complete nucleotide sequence of the principal allergen of the birch Bet v I, determined three times by single-stranded sequencing by means of sequenase, is found in FIGS. 10A–10B.

The length of the cDNA insert is 727 bases (FIGS. 10A–10B). Bases 1 to 11, i.e., the bases up to the cleavage site of the (T-deleted) Eco RI site at positions 11 to 15, and bases 739 to 744, i.e., the bases from the cleavage site of the (intact:) Eco RI site to the end of the sequence, are derived from the phage λgt11.

6.12.1. THE CODING SEGMENT

The sequence coding for Bet v I is characterized in FIG. 10 by the beginning and end of the amino acid sequence running parallel to the nucleotide sequence. The coded protein has a computed molecular weight of 17,570. The sequence starts with the base triplet ATG (position 65–67) coding for the amino acid methionine and ends with the base triplet TAA (position 545–547). Both these triplets are defined by the genetic code as "start" and "stop" codons, respectively. From ATG to TAA the reading frame is open.

The protein sequence obtained from this nucleotide sequence is identical with the AA sequence of the Bet v I protein sequenced up to amino acid 35 from the N-terminus.

The base triplets from position 311 to position 319 code for the amino acids Asn-Tyr-Ser. This amino-acid triplet involves a potential glycosylating site.

The DNA-sequence of Bet v I shows high homology to a pea disease resistance response gene as has been discussed above (Section 3).

6.12.2. THE NON-CODING SEGMENT

Regarding the non-coding segment from base 12 to base 64, the change in the Eco RI site in position 11 was brought about by deletion of a thymidine. As for the bases immediately in front of the starting codon (GCC ATC ATG), they constitute a "consensus" sequence described in the literature, in which the A located in the minus 3 position is constant, while the other bases may differ (Lutcke et al., *EMBO J.* 6:43, 1987).

Regarding the noncoding segment from base 548 to 744, the end of the cDNA is characterized by a 29-A polyadenyl sequence. The base sequence from position 693 to 698 (AAT AAA) is described in the literature as a consensus sequence essential for polyadenylation (M. Birnstiel et al., *Cell* 41:349, 1985)

From the data shown infra, it is concluded that the entire mRNA was cloned via cDNA. The reading frame is open, and the sequence indicated above is the complete sequence of the protein Bet v I.

What is claimed is:

1. A method for identifying a cDNA coding for an allergenic plant protein, said method comprising the steps of:

(a) preparing a cDNA clone bank from tissue of a plant suspected of producing an allergenic protein to which IgE antibodies in serum of an allergic individual are capable of binding;

(b) expressing said cDNA clone bank in a bacterial expression system to produce proteins;

(c) contacting the proteins produced from said cDNA clone bank with the serum of said allergic individual to form IgE antibody-protein complexes; and (d) determining which cDNA clones express a protein able to bind to said IgE antibodies by screening for said antibody-protein complexes with anti-IgE antibodies.

2. A method according to claim 1 wherein the allergenic protein is a pollen protein.

* * * * *